(12) United States Patent
Turecek et al.

(10) Patent No.: US 7,714,147 B2
(45) Date of Patent: May 11, 2010

(54) METHOD FOR PREPARING FMOC-BASED HYDROLYSABLE LINKERS

(75) Inventors: Peter Turecek, Klosterneuburg (AT); Juergen Siekmann, Vienna (AT); Christian Noe, Vienna (AT); Gerhard Stoiber, Palterndorf (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 12/215,217

(22) Filed: Jun. 25, 2008

(65) Prior Publication Data

US 2009/0005574 A1    Jan. 1, 2009

Related U.S. Application Data

(60) Provisional application No. 60/937,125, filed on Jun. 26, 2007.

(51) Int. Cl.
*C07D 207/24* (2006.01)

(52) U.S. Cl. .................................................. 548/528
(58) Field of Classification Search ...................... None
See application file for complete search history.

(56) References Cited

OTHER PUBLICATIONS

Corey, E.J. et al. J. Am. Chem. Soc. 94:17 (1972), pp. 6190-6191.*
Kocienski, Philip J. Protecting Groups, 3rd ed., 2005, Chapter 4—"Hydroxyl Protecting Groups," pp. 187-189 and 199.*
Tsubery et al. Journal of Biological Chemistry, 279 (37) pp. 38118-38124, 2004.*

* cited by examiner

*Primary Examiner*—Golam M. M. Shameem
*Assistant Examiner*—Alicia L Fierro
(74) *Attorney, Agent, or Firm*—Marshall, Gerstein & Borun LLP

(57) ABSTRACT

A novel process for the production of Fmoc (9H-fluoren-9-ylmethoxycarbonyl)-based compounds is provided, wherein a protecting group for the 9-hydroxymethyl group of the fluorene ring system is utilized. These compounds are useful for the modification of protein and peptide drugs.

8 Claims, No Drawings

METHOD FOR PREPARING FMOC-BASED HYDROLYSABLE LINKERS

CROSS REFERENCE TO RELATED APPLICATION

This application claims the benefit of priority to U.S. provisional application Ser. No. 60/937,125, filed Jun. 26, 2007, which is incorporated herein by reference in its entirety.

FIELD OF THE INVENTION

The present invention relates to the preparation of a hydrolysable linker, which is useful for the modification of protein and peptide drugs.

BACKGROUND OF THE INVENTION

Most peptide and protein drugs are short-lived and have often a short circulatory half-life in vivo. Considering that peptide and protein drugs are not absorbed orally, prolonged maintenance of therapeutically active drugs in the circulation is a desirable feature of obvious clinical importance.

An attractive strategy for improving clinical properties of protein or peptide drugs is a modification of protein or peptide drugs with polymers e.g. polyalkylene-oxides (Roberts et al., Advan Drug Rev. 54, 459-476 (2002)) or polysaccharides like Polysialic acid (Fernandes et al., Biochim Biophys Acta 1341, 26-34 (1997)), dextranes or hydroxylethyl starch. The modification with poly(ethylene glycol) (PEG) has been known for a while. However, modification of proteins with PEG often leads to reduction of the activity of the protein. Therefore alternative systems were developed allowing the releasable coupling of the polymer to the protein or peptide drug using hydrolysable or degradable chemical linkers (U.S. Pat. No. 6,515,100, U.S. Pat. No. 7,122,189, WO 04/089280, WO 06/138572). The protein-polymer conjugate can be regarded as a prodrug and the activity of the protein can be released from the conjugate via a controlled release mechanism. Using this concepts improved pharmacokinetic properties of the drug can be obtained (Zhao et al., Bioconjugate Chem. 17, 341-351 (2006)).

Therefore, WO 04/089280 suggested the use of a hydrolysable PEG-linker. (All documents cited in the specification are incorporated by reference.)

Tsubery et al., (J Biol. Chem. 279, 38118-38124 (2004)) demonstrated a hydrolysable PEG-linker for derivatization of proteins based on the Fmoc (9-fluorenylmethyl carbamate) group. A fluorene group is reacted with maleimidopropionic anhydride and N-hydroxysuccinimide, which is further reacted with poly(ethylene glycol) (PEG) and proteins by their amino groups. However, the synthesis of the hydrolysable linker, named MAL-FMS-OSU (9-Hydroxymethyl-2-(amino-3-maleimido-propionate)-7-sulfo fluorene N-hydroxysuccinimidyl carbonate), suffers from low yield and reduced reproducibility. The key problem with the synthesis according to Tsubery et al. is the introduction of the maleimide group by reaction of 9-Hydroxymethyl-2-amino fluorene with maleimido propionic acid anhydride. In this step undesired side reactions like esterification of the OH group in position 9 occurred. Thus, an improved synthesis containing an additional step for protection of the OH group was developed.

SUMMARY OF THE INVENTION

The present invention provides a new method for the synthesis of a compound of general formula 1:

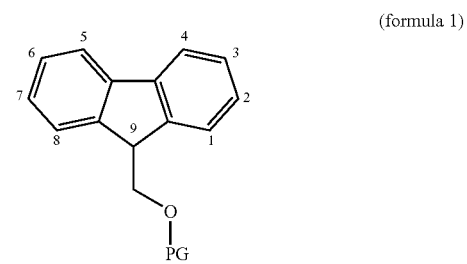

(formula 1)

wherein PG is a protecting group and at least one of position 1, 2, 3, 4, 5, 6, 7 or 8 is bound to radical Y.

Y is a radical containing a N-maleimidyl-moiety.

In addition to being bound to radical Y the compound of formula 1 may optionally be bound to radical X in at least one of the available position 1, 2, 3, 4, 5, 6, 7 or 8.

X is $-SO_3-R^3$.

$R^3$ is selected from the group consisting of hydrogen, $(C_1-C_8)$-alkyl and $(C_1-C_8)$-alkyl-$R^4$.

$R^4$ is a polymer.

Compounds of the invention are prepared according to a multi-step protocol wherein a protecting group for the 9-hydroxymethyl group of the fluorene ring system is being utilized. These derivatives can be further modified to yield an activated ester such as an succinimidyl ester.

DETAILED DESCRIPTION OF THE INVENTION

The present invention allows to overcome the above problems by a synthesis which utilizes a protecting group to yield a compound of formula 1. A compound of formula 1 is a suitable precursor for subsequent reaction steps yielding a hydrolysable linker, like MAL-FMS-OSU and other MAL-Fmoc-OSU-derivatives containing an active maleimide (MAL) and a N-hydroxysuccinimide (OSU=NHS) group and provides the desired products in high yield and purity. These linkers can be further modified with one or more polymers and can then be used to modify a peptide or protein drug.

The compounds of formula 1 are prepared starting from an amino-substituted fluorene. The new synthetic protocol introduces a protecting group for the hydroxylmethyl group at the 9 position of the fluorene in step 4 of the protocol shown below. The synthetic scheme below illustrates the preparation of a compound of formula 1 as an example:

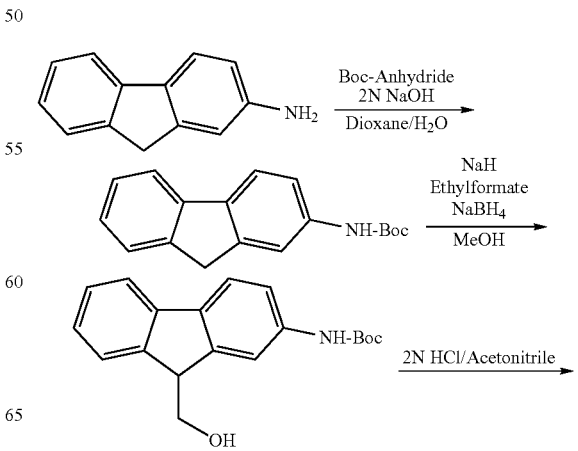

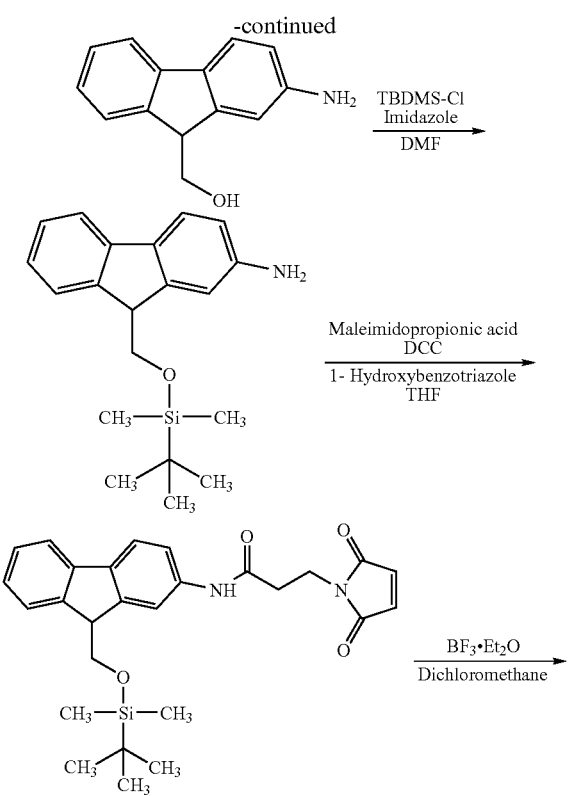

Further Reaction Steps:

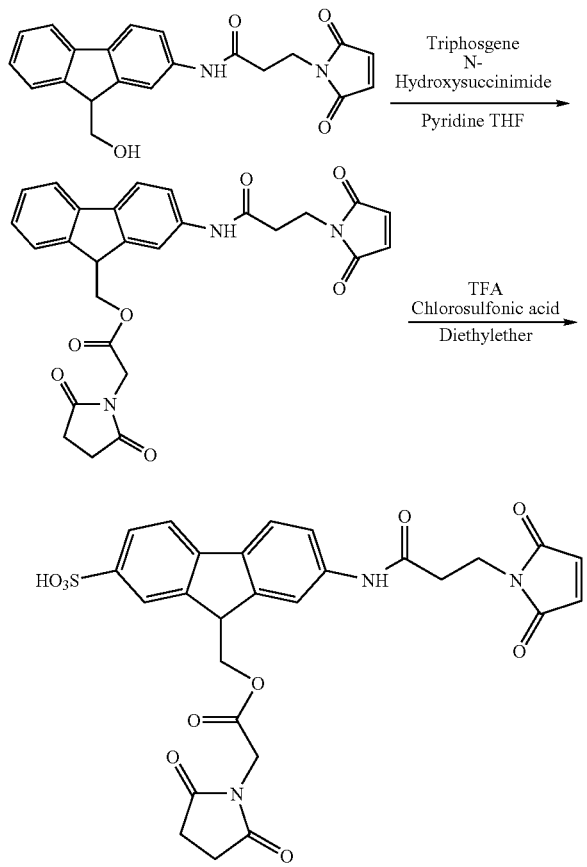

Step 1:

In a first step (see scheme above), an amine group of an amino-substituted fluorene is protected by a BOC group (tert-Butyloxycarbonyl), for example by reaction with BOC-anhydride or the like. Any other suitable protecting group (Greene et el., Protective Groups in organic synthesis, Jon Wiley & Sons, Inc., Third Edition, New York (1999)) for amines can be used. An additional example is the Z (Benzyloxycarbonyl) group.

Multi-amino-substituted fluorene derivatives can be used in a similar reaction in order to synthesize a compound of formula 1 having more than one radical Y in position 1, 2, 3, 4, 5, 6, 7 or 8.

Step 2:

In a second step a hydroxymethyl group is introduced at position 9 of the fluorene core, for example, by reaction with NaH or Lithiumdiisopropylamid (LDA) and ethylformiate and subsequent reaction with $NaBH_4$ or other reductive agents like DIBAL (Diisobutylaluminium hydride) in MeOH.

Step 3:

In a third step the BOC protecting group is cleaved, for example, with HCl $CF_3COOH$ or p-toluolsulfonic acid.

Step 4:

In a fourth step the 9-hydroxymethyl group is protected, for example, by reaction with a silyl halogenide such as tBDMS-Cl (Corey et al., J Am Chem. Soc. 94, 6190-6191 (1972)) or 4,4'-Trimethoxytritylchlorid.

In one embodiment the silyl halogenide is tBDMS-Cl (tert-butyldimethylsilyl chloride). Preferably, the reaction with tBDMS-Cl is performed with imidazole in DMF (dimethylformamide). The use of a silyl protecting group makes the molecule more lipophilic, thus facilitating the preparation of compounds, which are bound to more than one radical Y.

Step 5:

In a fifth step a N-maleimidyl-moiety is introduced, for example, by reacting the amino group with a maleimidoalkylic acid or a maleimidoalkylic acid anhydride.

The maleimidyl group is reactive towards thiole groups. Therefore, modified polymers such as PEG-SH can be covalently bound to the hydrolysable linker to yield a polymer-modified hydrolysable linker.

Step 6:

In this optional step, radical X ($—SO_3R^3$) is introduced in the fluorene ring system. This acidic group makes the compound more hydrophilic and allows to perform subsequent coupling reactions in aqueous solvents. In addition a sulfonic acid group allows the coupling of a second polymer by esterification with a OH-group of a polymer.

This procedure allows to introduce radical X to yield a compound of formula 1, comprising in addition to radical Y in position 1, 2, 3, 4, 5, 6, 7 or 8 also radical X in at least one of the available position 1, 2, 3, 4, 5, 6, 7 or 8.

In one embodiment, at least one radical X is bound to positions 2, 4, 5 and/or 7. In another embodiment, radical X is bound to position 7.

In another embodiment radical X ($—SO_3R^3$) is introduced in the fluorene ring system after step 4. If $—SO_3R^3$ is $—SO_3H$ the $—SO_3H$ group can be protected by esterification.

Further Reaction Steps:

After the condensation with maleimidoalkylic acid, the 9-hydroxymethyl can be deprotected by removing the protecting group (PG) to yield compounds of formula 2. Deprotection is preferably performed with $BF_3$, e.g. $BF_3.Et_2O$ (Boron tri-fuorid etherate).

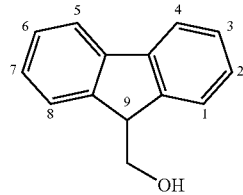

(formula 2)

MAL-FMS-OSU or its derivatives may be synthesized by reacting a compound of formula 2 with N-hydroxysuccinimide or its derivatives, such as N,N'-Disuccinimidyl carbonate. Reaction conditions for the formation of a succinimidyl-ester are well known in the art. A succinimidyl-modified compound for formula 2 can be further modified by reaction with SH-polymers and subsequently reacted with amino groups of peptide or protein drugs to yield conjugates of peptide or protein drugs having a hydrolysable linker containing a polymer.

The protocol exemplified above yields a compound of formula 1:

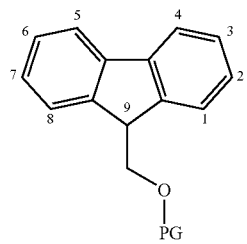

(formula 1)

wherein PG is a protecting group and at least one of position 1, 2, 3, 4, 5, 6, 7 or 8 is bound to radical Y.

Y is a N-maleimidyl-containing moiety.

Compounds of formula 1, which are substituted with at least one radical Y may also be bound to radical X in at least one of the available position 1, 2, 3, 4, 5, 6, 7 or 8.

X is $-SO_3-R^3$.

$R^3$ is independently selected from the group consisting of hydrogen, $(C_1-C_8)$-alkyl and $(C_1-C_8)$-alkyl-$R^4$.

"$C_1-C_8$-alkyl" refers to monovalent alkyl groups having 1 to 8 carbon atoms.

This term is exemplified by groups such as methyl, ethyl, propyl, butyl, hexyl and the like. Linear and branched alkyls are included.

$R^4$ is a polymer. Examples of polymers are poly(ethylene glycol) (PEG), polysialic acid (PSA), hydroxyalkyl starch (HAS) and the like.

In another embodiment the invention relates to a compound of formula 1, wherein PG is a silyl group. Examples of a silyl group are trimethylsilyl, triethylsilyl or t-butyldiphenylsilyl.

In another embodiment PG is a tert-butyldimethylsilyl group.

In one embodiment Y is:

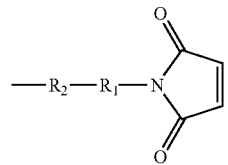

$R^1$ is at each occurrence independently a $(C_1-C_8)$-alkyl.

In one embodiment $R^1$ is at each occurrence independently selected from the group consisting of methyl, ethyl, propyl, butyl, and hexyl.

$R^2$ is independently selected from the group consisting of $-C(O)NR-$, $-C(O)NR-(C_1-C_8)$-alkyl-NR-, $-NRC(O)-$ and $-NRC(O)-(C_1-C_8)$-alkyl-NR, wherein R is independently either hydrogen or $C_1-C_8$-alkyl.

In one embodiment $R^2$ is $-C(O)NH-$.

In another embodiment $R^2$ is $-NHC(O)-$.

In one embodiment the compound of formula 1 is bound to radical Y in at least one of position 1, 2, 3 or 4.

In another embodiment the compound of formula 1, which is bound to radical Y in at least one of position 1, 2, 3, or 4 and is further bound to radical X in at least one of position 5, 6, 7, or 8.

In another embodiment the compounds of formula 1, which are substituted with at least one radical Y in at least one of position 2 or 3 may also be bound to radical X in at least one of position 7 or 8.

In another embodiment the compound of formula 1, which are substituted with at least one radical Y, radical X is bound to position 7.

In another embodiment the compounds of formula 1 are bound to radical Y in positions 2 and 7.

In another embodiment the compounds of formula 1 are bound to radical Y and radical X in positions 2 and 7, respectively.

In another embodiment the compound of formula 1 is:

The present invention is illustrated by the following examples without being limited thereto.

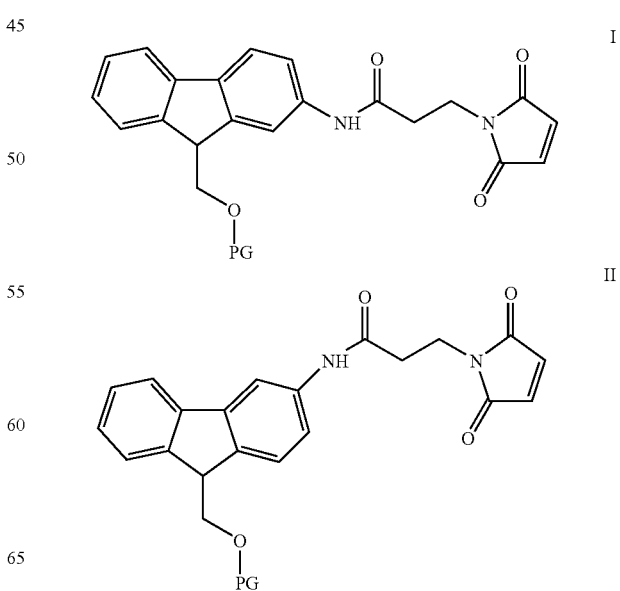

-continued

III

IV

V

VI

-continued

VII

VIII

IX

X

-continued

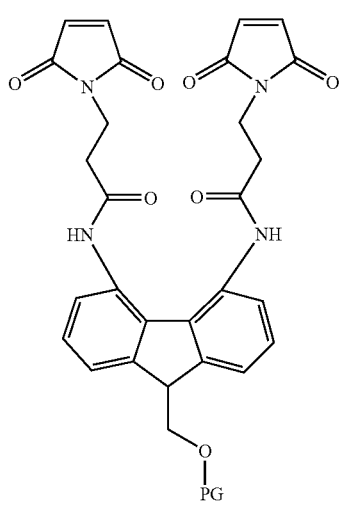

XI

EXAMPLES

MAL-Fmoc-OSu molecules can be synthesised according to the following protocol (Examples 1-8):

Example 1

Synthesis of 2-(Boc-amino)fluorene (Albericio et al., Synth Commun. 31, 225-32 (2001))

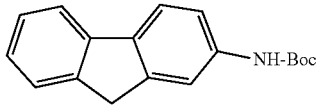

A suspension of 2-Aminofluorene (14.4 g, 79.7 mmol) was prepared in a mixture of 145 ml dioxane-$H_2O$ (2:1/V:V), cooled with an ice bath and 42.5 ml 2 N NaOH under gentle stirring. $Boc_2O$ (19.1 g, 87.7 mmol, 1.1 equiv) was then added and the stirring was continued at 25° C. The evolution of the reaction was followed by TLC [$R_f$=0.75 for 2-(Boc-amino) fluorene. $CHCl_3$-MeOH—HOAc (95:5:3)] and the pH was maintained between 9-10 by addition of 2 N NaOH. After 24 h TLC analysis showed the presence of 2-aminofluorene [$R_f$=0.60, $CHCl_3$-MeOH—HOAc (95:5:3)], so another 5.2 g $Boc_2O$ (23.8 mmol, 0.3 equiv) were added and the reaction was continued for additional 3 h until the total disappearance of the starting product. The suspension was acidified with 1 M $KHSO_4$ to pH 3. The solid was filtered and washed with 30 ml cold $H_2O$, 30 ml dioxane-$H_2O$ (2:1), 30 ml hexane and dried in vacuum. The product, a pale yellow powder (30.1 g, 90% yield) was shown to be pure by TLC [$R_f$=0.75; $CHCl_3$/MeOH/HOAc 95:5:3], and characterized by NMR.

$^1$H NMR (200 MHz/DMSO) δ=9.45 (1H; s; NH); 7.84-7.77 (3H; m; H1, H4, H5); 7.59-7.17 (4H; m; H2, H6-H8); 3.86 (2H; s; $CH_2$); 1.49 (9H, s, t-Bu)

$^{13}$C NMR (50 MHz/DMSO) δ=152.8 (Amid-C); 143.8 (C9a); 142.6 (C8a); 141.2 (C4b); 138.7 (C2); 135.2 (C4a); 126.7 (C6); 125.8 (C7); 124.9 (C8); 120.0 (C4); 119.2 (C5); 116.9 (C3); 114.8 ($C_1$); 79.02 ($CH_2$); 39.5 (Cq t-Bu); 28.2 (3×$CH_3$ t-Bu)

Example 2

Synthesis of 9-Hydroxymethyl-2-(Boc-amino) fluorene (Albericio et al., Synth Commun. 31, 225-32 (2001))

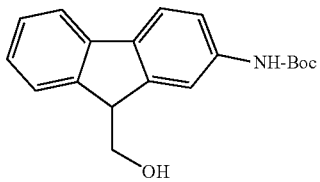

A solution of 2-(Boc-amino) fluorene (13.49 g, 47.9 mmol) in 140 ml dry THF (freshly distilled from sodium) was carefully added to a suspension of 6.3 g 60% NaH (160 mmol, 3.3 equiv) in 20 ml dry THF under argon atmosphere. Gas evolution and spontaneous warming were observed. After the complete addition of 2-(Boc-amino)fluorene the reaction mixture was stirred for 1 h at 40° C. Then the reaction mixture was cooled to room temperature and 9.7 ml ethyl formate (120 mmol, 2.5 equiv) were slowly added to avoid vigorous hydrogen bubbling. The initially thick, light brown suspension rapidly clarified to a dark brown solution upon addition of ethyl formate and was stirred for 1 h. The evolution of the reaction was followed by TLC [Rf=0.52 for the intermediate product, $CHCl_3$-MeOH—HOAc (95:5:3)]. The reaction was quenched with ice chips and 100 ml $H_2O$ and the organic solvent was removed by rotary evaporation. To the aqueous phase 10 ml 2 N NaOH were added and it washed with 3×50 ml diethylether, cooled in an ice bath and acidified with 25 ml glacial HOAc until pH 5. The off-white precipitate that then appeared was dissolved in 300 ml EtOAc. The aqueous phase was extracted with 50 ml EtOAc and the organic phase was washed with 2×75 ml sat. $NaHCO_3$ and 1×75 ml brine and dried over $Na_2SO_4$. The solvent was eliminated under reduced pressure.

9-Formyl-2-(Boc-amino) fluorene was suspended in 100 ml methanol and 2.0 g $NaBH_4$ [52.9 mmol, 1.1 equiv with respect to the starting 2-(Boc-amino) fluorene] was added portion wise. The suspension that rapidly cleared up was magnetically stirred until the starting product disappeared for 4 h at room temperature [TLC, $R_f$=0.57, PE:MTBE (1:2)]. The reaction mixture was diluted with 300 ml $H_2O$ and acidified with 15 ml glacial HOAc to pH 5.0, and the precipitate was directly dissolved in 150 ml EtOAc. The organic phase was washed with 3×50 ml sat. $NaHCO_3$ and 1×50 ml brine and dried over anhydrous $Na_2SO_4$. The solvent was rotary evaporated to give a solid, which could be used without further purification. The product was analyzed by NMR (13.1 g, 88% yield).

$^1$H NMR (200 MHz/DMSO) δ=9.42 (1H; s; NH); 7.87 (1H; s; H1); 7.79-7.66 (2H; m; H4, H5); 7.61 (1H; d; J=7.71 Hz; H8); 7.48-7.15 (3H, m, H3, H6, H7); 5.07 (1H, t, J=4.80 Hz; OH); 4.00-3.88 (1H; m; H9); 3.82-3.63 (2H; m; $CH_2$); 1.49 (9H; s; t-Bu)

$^{13}$C NMR (50 MHz/DMSO) δ=152.88 (Amid-C); 146.05 (C9a); 144.90 (C8a); 140.81 (C4b); 138.64 (C2); 134.90 (C4a); 127.13 (C6); 125.85 (C7); 125.05 (C8); 119.93 (C4);

119.16 (C5); 117.47 (C3); 115.24 ($C_1$); 79.00 (Cq t-Bu); 63.85 ($CH_2$); 50.19 (C9); 28.20 (3×$CH_3$ t-Bu)

Example 3

Synthesis of 9-Hydroxymethyl-2-amino fluorene

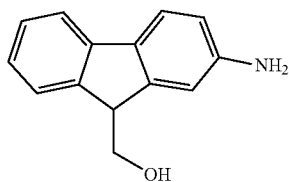

13.0 g 9-Hydroxymethyl-2-(Boc-amino)fluorene was dissolved in 110 ml acetonitrile and stirred under reflux. 42 ml 2 N HCl (2.0 equiv, 84 mmol) was added drop-wise. The reaction mixture was stirred under reflux for 45 min. The reaction mixture was cooled to room temperature and the reaction was monitored by TLC [$R_f$=0.1 PE-MTBE (1:2)]. The solvent was partially eliminated by rotary evaporation and the residue was dissolved in 70 ml 2 N HCl. The solution was carefully washed with 2×50 ml MTBE. The aqueous phase was adjusted to pH 9 by $Na_2CO_3$ and extracted with 2×70 ml EtOAc. The organic phase was washed with 50 ml brine and dried over $Na_2SO_4$. The solvent was eliminated by rotary evaporation. The product was used without further purification. The structural identity was verified by NMR (8.76 g, 99% yield).

$^1$H NMR (200 MHz/DMSO) δ=7.69-7.40 (3H; m; 3×Ar—H); 7.37-7.02 (2H; m; 2×Ar—H); 6.87 (1H; s; Ar—H); 6.68 (1H; d; J=8.34 Hz; Ar—H); 5.19 (2H; s; $NH_2$); 5.03 (1H; t; J=4.93 Hz; OH); 3.93-3.58 (3H; m; H9, $CH_2$)

$^{13}$C NMR (50 MHz/DMSO) δ=148.36 (Ar—Cqu); 146.81 (Ar—Cqu); 143.97 (Ar—Cqu); 141.87 (Ar—Cqu); 129.03 (Ar—Cqu); 126.92 (Ar—CH); 124.85 (Ar—CH); 124.24 (Ar—CH); 120.40 (Ar—CH); 117.81 (Ar—CH); 113.00 (Ar—CH); 110.76 (Ar—CH); 64.27 ($CH_2$); 49.90 (CH)

Example 4

Synthesis of tert-Butyldimethylsiloxy-9-methyl-2-aminofluorene

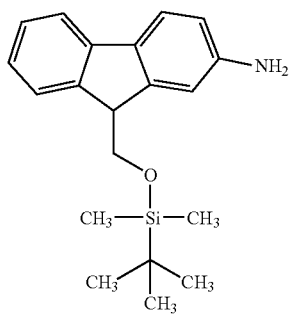

5.91 g Imidazole (86.8 mmol, 2.1 equiv) was dissolved in 24 ml dry DMF and stirred 10 min in an iced bath under argon atmosphere. 7.47 g tert-Butyldimethylsilyl chloride (49.6 mmol, 1.2 equiv) dissolved in dry DMF was added. After 15 min stirring on ice 8.73 g 9-Hydroxymethyl-2-amino fluorene (41.3 mmol) dissolved in 40 ml dry DMF was added drop wise under cooling and argon atmosphere. The reaction was continued 15 min on ice and then at room temperature. The reaction was monitored by TLC [title product $R_f$=0.6, PE-MTBE (1:2)]. After 2 hours the starting product [$R_f$=0.1 PE-MTBE (1:2)] had disappeared and the reaction mixture was diluted with 400 ml $CH_2Cl_2$ and 100 ml 5% $NaHCO_3$ was added. The organic phase was washed with 5×200 ml $H_2O$ and dried over $Na_2SO_4$. $CH_2Cl_2$ was eliminated by rotary evaporation and DMF was eliminated by azeotropic distillation with toluene. The residual brown oil (13.4 g, 99% yield) was analyzed by NMR and was used without further purification.

$^1$H NMR (200 MHz/DMSO) δ=7.67-7.40 (3H; m; 3×Ar—H); 7.34-7.00 (2H; m; 2×Ar—H); 6.81 (1H; s; 1×Ar—H); 6.59 (1×; dd; J=8.02 Hz & 1.83 Hz; 1×Ar—H); 5.19 (2H; s; $NH_2$); 3.97-3.76 (2H; m; $CH_2$); 3.75-3.57 (1H; m; CH); 0.88 (9H; s; 3×$CH_3$); 0.03 (6H; s; 2×$CH_3$)

$^{13}$C NMR (50 MHz/DMSO) δ=148.40 (Ar—Cqu); 145.81 (Ar—Cqu); 143.67 (Ar—Cqu); 141.88 (Ar—Cqu); 129.08 (Ar—Cqu); 127.10 (Ar—CH); 124.97 (Ar—CH); 124.16 (Ar—CH); 120.47 (Ar—CH); 117.87 (Ar—CH); 113.22 (Ar—CH); 110.58 (Ar—CH); 66.04 ($CH_2$—OH); 49.60 (C9); 25.88 (3×$CH_3$; t-Bu); 18.04 (Cqu; t-Bu), −5.04 (2$CH_3$; Si—$CH_3$)

Example 5

Synthesis of tert-Butyldimethylsiloxy-9-methyl-2-(amino-3-maleimidopropionate) fluorene

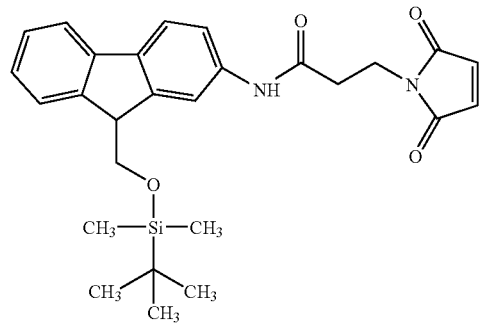

To a solution of 13.5 g 9-tert-Butyldimethylsiloxymethyl-2-aminofluorene (41.5 mmol) in dry THF (freshly distilled from sodium) 9.42 g N,N'-dicyclohexylcarbodiimide (75.7 mmol, 1.1 equiv) and 651 mg 1-hydroxybenzotriazole (4.8 mmol, 0.1 equiv) were added. 13.5 g (41.5 mmol, 1.1 equiv) 3-maleimidopropionic acid was dissolved in 50 ml dry THF and added drop-wise. The reaction mixture was stirred at room temperature over night under argon atmosphere and the product formation was monitored by TLC [starting material $R_f$=0.6, title product $R_f$=0.18, PE-MTBE (1:2)].

As soon as the starting material could not be detected, dicyclohexylurea was filtered out and THF was eliminated by rotary evaporation. The residual solid was dissolved in 200 ml $CH_2Cl_2$, washed with 50 ml 5% $NaHCO_3$ and 50 ml brine and dried over $Na_2SO_4$. The brown crystals were digerated in 20 ml MTBE. After filtration the residue was washed with small portions of MTBE until the washing solution maintained colorless. The yellow crystals (10.5 g, 53% yield) were analyzed by NMR.

¹H NMR (200 MHz/DMSO) δ=10.06 (1H; s; NH); 7.92 (1H; s; H1); 7.82-7.70 (2H; m; H4 & H5); 7.62 (1H; d; J=7.20 Hz; H3); 7.49 (1H; d; J=8.08 Hz; H8); 7.41-7.18 (2H; m; H6 & H7); 7.03 (2H; s; 2×Mal-CH); 4.02 (1H; t; J=6.63 Hz; H9); 3.95-3.66 (4H; m; Prop-CH$_2$—N & CH$_2$—OTBDMS); 2.61 (2H; t; J=7.07 Hz; Prop-CH$_2$—C=O); 0.84 (9H; s; 3×t-Bu CH$_3$); 0.10-0.56 (6H; m; 2×CH$_3$—Si)

¹³C NMR (50 MHz/DMSO) δ=170.81 (C=O Mal); 168.30 (C=O Amid); 145.12 (C9a); 144.62 (C8a); 140.68 (C4b); 138.05 (C2); 136.02 (C4a); 134.62 (2×CH Mal); 127.34 (C6); 126.02 (C7); 125.15 (C8); 119.99 (C4); 119.37 (C5); 118.63 (C3); 116.31 (C$_1$); 65.54 (CH$_2$OTBDMS); 49.85 (C9); 35.01 (Prop-CH$_2$—N); 33.91 (Prop-CH$_2$—CO); 25.84 (3×CH$_3$ t-Bu); 18.01 (Cqu t-Bu); −5.40 (CH$_3$—Si); −5.44 (CH$_3$—Si)

Example 6

Synthesis of
9-Hydroxymethyl-2-(amino-3-maleimidopropionate)
fluorene

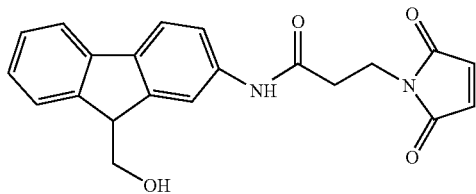

10.3 g tert-Butyldimethylsiloxy-9-methyl-2-(amino-3-maleimidopropionate) fluorene (21.6 mmol) was dissolved in 230 ml CH$_2$Cl$_2$ under argon atmosphere. 35 ml boron trifluoride etherate were added drop-wise over 30 min. The reaction was monitored by TLC [starting material R$_f$=0.6, title product R$_f$=0.38, CH$_2$Cl$_2$-Methanol (10:1)]. As soon as the starting material had disappeared the solution was hydrolyzed with sat. NaHCO$_3$ solution. The resulting crystals were filtered. The organic phase of the mother liquor was evaporated. This residue and the filter cake were re-dissolved in 250 ml EtOAc and 120 ml 5% NaHCO$_3$. The organic phase was washed with 1×50 ml 5% NaHCO$_3$, 50 ml H$_2$O and 50 ml brine and dried over Na$_2$SO$_4$. The solvent was eliminated by rotary evaporation. The structure of the product was verified by NMR and mass spectroscopy.

¹H NMR (200 MHz/DMSO) δ=10.09 (1H; s; NH); 7.88 (1H; s; H1); 7.82-7.69 (2H; m; H4 & H5); 7.66-7.52 (2H; m; H3 & H8); 7.41-7.17 (2H; m; H6 & H7); 7.03 (2H; s; 2×Mal-CH); 5.09 (1H; t; J=4.93 Hz; OH); 5.08 (1H; t; J=6.06 Hz; H9); 3.97-3.53 (4H; m; Prop-CH$_2$—N & CH$_2$—OH); 2.61 (2H; t; J=6.82 Hz; Prop-CH$_2$—C=O)

¹³C NMR (50 MHz/DMSO) δ=170.82 (C=O Mal); 168.38 (C=O Amid); 146.00 (C9a); 144.89 (C8a); 140.63 (C4b); 138.05 (C2); 135.92 (C4a); 134.62 (2×CH Mal); 127.16 (C6); 126.09 (C7); 125.03 (C8); 119.93 (C4); 119.33 (C5); 118.39 (C3); 116.36 (C$_1$); 63.86 (CH$_2$OH); 50.14 (C9); 35.07 (Prop-CH$_2$—N); 33.92 (Prop-CH$_2$—CO)

ESI-MS: found: (M+Na)$^+$: 385.2. calculated: (M+Na)$^+$: 385.

Example 7

Synthesis of
9-Hydroxymethyl-2-(amino-3-maleimidopropionate)
fluorene N-hydroxysuccinimidyl carbonate

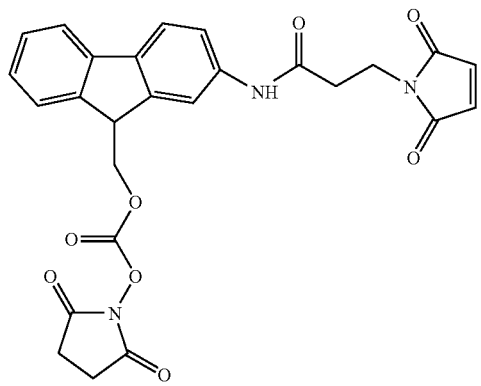

From a solution of 1.8 g pyridine in 7.3 ml abs THF 1.7 ml (5.1 mmol) were added drop wise to a stirred solution of 0.93 g 9-Hydroxymethyl-2-(amino-3-maleimidopropionate) fluorene (2.6 mmol) and 1.1 g triphosgene (3.6 mmol, 1.4 equiv) in 75 ml dry THF (freshly distilled from sodium). After 40 min the precipitated pyridine hydrochloride salt was filtered out over celite, and the THF was removed by rotary evaporation. The oil obtained was dissolved in 75 ml dry tetrahydrofuran with 1.1 g N-hydroxysuccinimide (13.6 mmol, 5.3 equiv). 2.6 ml of the pyridine solution (8.2 mmol) were then added, and the solution was stirred for 40 min. Some additional precipitated pyridine hydrochloride salt was filtered out over celite, and the THF was removed by rotary evaporation. The oil obtained was dissolved in 70 ml chloroform and washed with 4×40 ml 0.1N HCl, 3×50 ml of an aqueous 5% NaHCO$_3$ solution, then with 1×40 ml water, 40 ml brine and dried over Na$_2$SO$_4$. The chloroform was removed by rotary evaporation. Structural identity was verified by NMR and mass spectroscopy.

¹H NMR (500 MHz/CDCl$_3$) δ=8.35 (1H; s; NH); 8.00-7.95 (1H; m; H3); 7.71-7.65 (2H; m; H4 & H5); 7.50-7.46 (1H; d; J=7.25 Hz; H8); 7.42-7.36 (2H; m; H1 & H6); 7.30-7.25 (1H; m; H7); 6.69 (2H; s; 2×Mal-CH); 4.66 (1H; dd; J=10.40 Hz & 5.99 Hz; H$_a$—CH$_2$O); 4.14 (1H; t; J=10.09 Hz; H$_b$—CH$_2$O); 4.27 (1H; dd; J=9.46 Hz & 5.99 Hz; H9); 3.95 (2H; t; J=7.09 Hz; Prop-CH$_2$—N); 2.86 (4H; s; 2× Succ-CH$_2$); 2.80-2.54 (2H; m; Prop-CH$_2$—C=O)

¹³C NMR (125 MHz/CDCl$_3$) δ=170.53 (C=O Mal); 168.21 (C=O Amid); 151.41 (C=O Carbonate); 143.79 (C2); 141.13 (C9a); 140.94 (C8a); 137.36 (C4b); 137.11 (C4a); 134.20 (2×CH Mal); 128.33 (C6); 126.82 (C7); 124.62 (C8); 120.63 (C4); 120.23 (C3); 119.96 (C5); 116.50 (C$_1$); 72.67 (CH$_2$O); 46.49 (C9); 35.62 (PropCH$_2$—N); 34.15 (Prop-CH$_2$—CO); 25.47 (2×Succ-CH$_2$)

ESI-MS (calculated): (M+H)$^+$: 504; (M+Na)$^+$: 526.
ESI-MS (found): (M+H)$^+$: 504.1; (M+Na)$^+$: 526.1.

Example 8

Synthesis of 9-Hydroxymethyl-2-(amino-3-maleimidopropionate)-7-sulfo fluorene N-hydroxysuccinimidyl carbonate To a solution of 1.2 g 9-Hydroxymethyl-2-(amino-3-maleimidopropionate) fluorene N-hydroxysuccinimidyl carbonate (2.1 mmol) in 60 ml trifluoroacetic acid 7 ml chlorosulfonic acid was added. After 30 min the reaction mixture was cooled to 4° C. and 350 ml cold diethylether was added. The precipitated product was filtered and washed twice with diethylether and dried in vacuum.

Structural identity was verified by mass spectroscopy.
ESI-MS (found): (M+H)$^+$: 583.9
ESI-MS (calculated): (M+H)$^+$: 583.

The synthesis of MAL2-Fmoc-OSu starting from 2,7 Diaminofluorene is illustrated in Example 9.

Example 9

Synthesis of 9-Hydroxymethyl-2,7-Di-(amino-3-maleimidopropionate) fluorene N-hydroxysuccinimidyl carbonate 9-Hydroxymethyl-2,7-Di-(amino-3-maleimidopropionate) fluorene N-hydroxysuccinimidyl carbonate is prepared under the conditions as described in Examples 1-8. The amino groups in 2,7-Diaminofluorene are protected with BOC$_2$O as described by Albericio et al., Synth Commun. 31, 225-32 (2001). Then the formyl-group is introduced in position 9 by reaction of Lithiumdiisopropylamide (LDA) and ethylformiate. The aldehyde obtained is reduced with sodiumborhydride to the corresponding alcohol to form 9-Hydroxymethyl-2,7-di-(Boc-amino)fluorene. Subsequently the BOC protecting groups are cleaved with 2N HCl in CH$_3$CN and 9-Hydroxymethyl-2,7-diaminofluorene is obtained. Then the OH-group is protected by reaction with tert.-Butyldimethylsilylchloride as described in Example 5 to form tert-Butyldimethylsiloxy-9-methyl-2,7-diaminofluorene. Then the reaction of the free amino groups with maleimidopropionic acid in the presence of N,N'-dicyclohexylcarbodiimide and hydroxybenzotriazole is performed and tert-Butyldimethylsiloxy-9-methyl-2,7-di-(amino-3-maleimidopropionate) fluorene is obtained. After deprotection of the OH group in position 9 with Boron trifluoride etherate 9-Hydroxymethyl-2,7-di-(amino-3-maleimidopropionate) fluorene is formed. Finally the reaction with Triphosgene and N-hydroxysuccinimide is carried out and 9-Hydroxymethyl-2,7-di-(amino-3-maleimidopropionate) fluorene N-hydroxysuccinimidyl carbonate is prepared.

The invention claimed is:

1. A method of preparing a compound according to formula 1:

(formula 1)

wherein PG is a silyl protecting group and at least one of position 1, 2, 3, 4, 5, 6, 7 or 8 is bound to radical Y;
Y is a radical containing a N-maleimidyl-moiety having a structure $R^1$ is a (C$_1$-C$_8$)-alkyl;
$R^2$ is selected from the group consisting of —C(O)NR—, —C(O)NR—(C$_1$-C$_8$)-alkyl-NR—, —NRC(O)— and —NRC(O)—(C$_1$-C$_8$)-alkyl-NR, wherein R is independently either hydrogen or C$_1$-C$_8$-alkyl;
at least one of an available position 1, 2, 3, 4, 5, 6, 7 or 8 is optionally bound to radical X;
X is —SO$_3$R$^3$;
$R^3$ is independently selected from the group consisting of hydrogen, (C$_1$-C$_8$)-alkyl and (C$_1$-C$_8$)-alkyl-R$^4$; and
$R^4$ is a polymer;
said method comprises the steps of
reacting the 9-hydroxymethyl group of a compound of formula 2:

(formula 2)

wherein at least one of position 1, 2, 3, 4, 5, 6, 7 or 8 is bound to an amine, with a silyl protecting reagent introducing PG, and subsequently reacting said compound with an N-maleimidyl reagent to form the compound of formula (1).

2. The method according to claim 1, wherein said silyl protecting reagent is a silyl halide.

3. The method according to claim 2, wherein said halide is tert-butyldimethylsilyl chloride (tBDMS-Cl).

4. The method according to claim 3, wherein said reaction with tBDMS-Cl is performed with imidazole in dimethylformamide (DMF).

5. The method according to claim 4, wherein said N-maleimidyl-reagent is maleimidoalkylic acid.

6. The method according to claim 3, wherein at least one of an available position 1, 2, 3, 4, 5, 6, 7 or 8 is bound to radical X.

7. A compound of the formula 1,

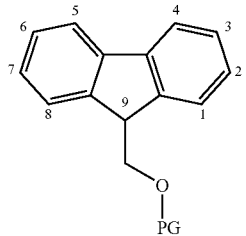

(formula 1)

wherein PG is a silyl protecting group and at least one of position 1, 2, 3, 4, 5, 6, 7 or 8 is bound to radical Y; and at least one of an available position 1, 2, 3, 4, 5, 6, 7 or 8 is optionally bound to radical X;

Y is a N-maleimidyl-containing moiety having a structure:

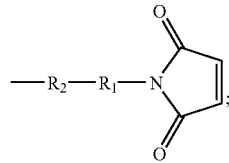

X is —$SO_3R^3$—;

$R^3$ is independently selected from the group consisting of hydrogen, ($C_1$-$C_8$)-alkyl and ($C_1$-$C_8$)-alkyl-$R^4$;

$R^4$ is a polymer;

$R^1$ is a ($C_1$-$C_8$)-alkyl; and $R^2$ is selected from the group consisting of —C(O)NR—, —C(O)NR—($C_1$-$C_8$)-alkyl-NR—, NRC(O)— and —NRC(O)—($C_1$-$C_8$)-alkyl-NR—, wherein R is hydrogen or $C_1$-$C_8$-alkyl.

8. The compound according to claim 7, wherein PG is a t-butyldimethylsilyl protecting group.

* * * * *